US010779782B2

(12) United States Patent
Risher-Kelly

(10) Patent No.: US 10,779,782 B2
(45) Date of Patent: *Sep. 22, 2020

(54) APPARATUS AND METHOD FOR MECHANICALLY PROVIDING POWER TO A GENERATOR ON A CONTINUOUS ROTATABLE ROTOR OF AN X-RAY SCANNER

(71) Applicant: Medtronic Navigation, Inc., Louisville, CO (US)

(72) Inventor: Clifford M. Risher-Kelly, Wells, ME (US)

(73) Assignee: Medtronic Navigation, Inc., Louisville, CO (US)

( * ) Notice: Subject to any disclaimer, the term of this patent is extended or adjusted under 35 U.S.C. 154(b) by 185 days.

This patent is subject to a terminal disclaimer.

(21) Appl. No.: 15/817,995

(22) Filed: Nov. 20, 2017

(65) Prior Publication Data

US 2018/0085076 A1    Mar. 29, 2018

Related U.S. Application Data

(63) Continuation of application No. 14/672,391, filed on Mar. 30, 2015, now Pat. No. 9,820,708.

(51) Int. Cl.
*H05G 1/10* (2006.01)
*A61B 6/00* (2006.01)
(Continued)

(52) U.S. Cl.
CPC .......... *A61B 6/4476* (2013.01); *A61B 6/4435* (2013.01); *A61B 6/56* (2013.01);
(Continued)

(58) Field of Classification Search
CPC ..... A61B 6/035; A61B 6/4435; A61B 6/4476; A61B 6/56; A61B 6/032; A61B 6/4488;
(Continued)

(56) References Cited

U.S. PATENT DOCUMENTS 4,200,797 A    4/1980  Bax
4,365,339 A    12/1982 Pavkovich et al.
(Continued)

FOREIGN PATENT DOCUMENTS

WO    2004045412 A1    6/2004
WO    2015088535 A1    6/2015

OTHER PUBLICATIONS

International Preliminary Report on Patentability dated Oct. 12, 2017 in corresponding International Application No. PCT/US2016/023060.

(Continued)

*Primary Examiner* — Irakli Kiknadze
(74) *Attorney, Agent, or Firm* — Harness Dickey

(57) ABSTRACT

A system including an x-ray scanner gantry having: a housing; a gantry gear; a rotor; a generator mounted on the rotor; and first and second generator gears connected to or engaged with one or more axles of the generator. The second generator gear is engaged with the gantry gear. A motor rotates the intermediate gear via a motor gear. A second actuator actuates the motor gear to engage the motor with the rotor. A control module operates in first and second modes and: while in the first mode, engages the intermediate gear to the first generator gear via the first actuator to rotate, via the motor gear, the intermediate gear and as a result the first generator gear; and while in the second mode, engage the motor to the rotor via the second actuator to rotate, via the motor gear, the rotor and as a result the second generator gear.

19 Claims, 4 Drawing Sheets

(51) Int. Cl.
*H02K 7/108* (2006.01)
*H02K 7/116* (2006.01)
*H02P 9/06* (2006.01)
*A61B 6/03* (2006.01)

(52) U.S. Cl.
CPC ............. *H02K 7/108* (2013.01); *H02K 7/116* (2013.01); *H02P 9/06* (2013.01); *H05G 1/10* (2013.01); *A61B 6/035* (2013.01)

(58) Field of Classification Search
CPC ..... A61B 6/5205; A61B 6/4447; A61B 6/541; A61B 6/4233; A61B 6/027; A61B 6/44; A61B 6/461; A61B 6/488; A61B 6/5258; A61B 6/4405; A61B 6/4014; A61B 6/4275; A61B 6/505; A61B 6/0457; A61B 2560/0406; A61B 5/0555; A61B 5/704; A61B 6/04; A61B 6/0407; A61B 6/102; A61B 6/547; A61B 6/105; A61B 6/06; A61B 6/4021; A61B 6/4085; A61B 6/4452; A61B 6/4411; A61B 6/467; A61B 6/466; A61B 6/4441; H02K 7/108; H02K 7/116; H02P 9/06; H05G 1/10; H05G 1/02; H05G 1/24; H05G 1/48; H05G 1/70; G06T 2207/30101; G06T 11/006; G06T 2207/10081; G06T 2207/10121; G06T 2207/20224; G06T 2211/421; G06T 2211/424; G06T 5/50; G06T 7/0012; G06T 7/0016; G06T 7/20; H02J 7/1492; A61N 2005/1052; A61N 5/1049; A61N 2005/005; A61N 2005/1054; A61N 2005/1055; A61N 2005/1061; A61N 2005/1091; A61N 2005/1094; A61L 36/4233; A61L 36/4452; A61L 36/035; A61L 36/4435; A61L 36/4476; A61L 36/4085; A61L 36/4021; A61L 36/4447; A61L 36/466; A61L 36/467; A61L 36/5205; G01T 1/1603; G01T 1/1606; G01T 1/2985; G21K 1/025; G21K 1/046
USPC ...................................... 378/4, 15, 101, 102
See application file for complete search history.

(56) References Cited

U.S. PATENT DOCUMENTS

| | | | |
|---|---|---|---|
| RE38,560 E | 8/2004 | Hug et al. | |
| 6,940,941 B2 | 9/2005 | Gregerson et al. | |
| 7,001,045 B2 | 2/2006 | Gregerson et al. | |
| 7,188,998 B2 | 3/2007 | Gregerson et al. | |
| 7,338,207 B2 | 3/2008 | Gregerson et al. | |
| 7,490,982 B2 | 2/2009 | Gregerson et al. | |
| 7,905,659 B2 | 3/2011 | Gregerson et al. | |
| 8,308,361 B2 | 11/2012 | Gregerson et al. | |
| 8,746,973 B2 | 6/2014 | Gregerson et al. | |
| 9,820,708 B2 * | 11/2017 | Risher-Kelly | A61B 6/4435 |
| 2005/0135560 A1 * | 6/2005 | Dafni | A61B 6/56 378/101 |
| 2007/0023699 A1 | 2/2007 | Yamashita et al. | |
| 2015/0196262 A1 * | 7/2015 | Grady | A61B 6/4405 378/42 |

OTHER PUBLICATIONS

International Search Report and Written Opinion dated Jun. 21, 2016 in corresponding International Application No. PCT/US2016/023060.
Australian Examination Report for Application No. 2016244059 dated Dec. 4, 2019.
Office Action dated May 7, 2020 in corresponding/related Chinese Application No. 201680029904.4.

* cited by examiner

APPARATUS AND METHOD FOR MECHANICALLY PROVIDING POWER TO A GENERATOR ON A CONTINUOUS ROTATABLE ROTOR OF AN X-RAY SCANNER

CROSS-REFERENCE TO RELATED APPLICATIONS

This application is a continuation of U.S. patent application Ser. No. 14/672,391 filed on Mar. 30, 2015. The entire disclosure of the above application is incorporated herein by reference.

FIELD

The present disclosure relates to continuously rotating x-ray imaging systems, and more particularly to powering a generator on a rotor of an x-ray scanner.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the patient based on images of the patient, which can be acquired using an x-ray scanner having an imaging system. The images may be acquired prior to or during the procedure. The imaging system may be, for example, an O-Arm or C-Arm imaging system. The images may be fluoroscopic or radiographic images depending on an operating mode of the imaging system.

The acquired images of the patient can assist a surgeon in planning and performing the procedure. A surgeon may select a two dimensional image or a three dimensional image representation of the patient. The images can assist the surgeon in performing a procedure with a less invasive technique by allowing the surgeon to view the anatomy of the patient without removing overlying tissue (including dermal and muscular tissue) when performing a procedure.

An O-Arm imaging system includes an 'O'-shaped gantry and a 'O'-shaped rotor. A C-Arm imaging system includes a 'C'-shaped gantry and a 'C'-shaped rotor. Each of these imaging systems typically includes an x-ray source and a x-ray detector mounted opposite each other on the corresponding rotor. Each of the x-ray sources generates x-rays, which are directed at a subject. Each of the x-ray detectors detects the x-rays subsequent to the x-rays passing through the subject.

Although traditional O-Arm and C-Arm imaging systems were capable of taking 360 degrees of images around a subject, the imaging systems were incapable of rotating the rotors more than 360 degrees (or one full rotation). Thus, the systems were incapable of continuously rotating the rotors in a same direction. Once the rotors were rotated 360 degrees, the rotors were rotated back in an opposite direction to the initial (or 0° position). An imaging system having a rotor that is 360° rotation limited typically includes cables, which are used to (i) provide power to device on the rotor, and/or (ii) transfer communication signals between the devices on and off of the rotor. The cables may extend in the corresponding gantry and may be pulled around the rotor during imaging and retracted to an initial state when the rotor is returned to an initial position.

It is advantageous to provide an imaging system with a continuously rotating rotor such that the rotor is not 360° rotation limited. This is especially true when imaging blood vessels. For this reason, certain imaging systems are available that are capable of continuously rotating a corresponding rotor in a same direction. The imaging systems that are continuous rotor rotation capable include an x-ray source, an x-ray detector, and a generator, which are mounted on the rotor. The generator converts a low-voltage (e.g., 400 volts (V)) to a high-voltage (e.g., 150 kilo-volts (kV)). The high-voltage is provided to the x-ray source. In order to provide power to the generator, slip rings are used to pass, for example, the 400V of power from a stationary power source in the gantry to the generator, which is on the rotor. The slip rings are expensive to purchase and maintain due to the required scheduled maintenance of the slip rings.

As another example and instead of using slip rings, inductive coupling may be used to convert the low-voltage to the high-voltage. This includes placing secondary coils around a rotor of a gantry and a stationary primary coil inductively transferring power from the secondary coils to the primary coil. Power received by the secondary coils is provided to the device (e.g., an x-ray source) on the rotor. This type of imaging system include a large number of coils, is complex, and can require additional energy to rotate the rotor due to the added weight of the secondary coils and corresponding circuitry.

SUMMARY

This section provides a general summary of the disclosure, and is not a comprehensive disclosure of its full scope or all of its features.

According to various embodiments, provided is a system that includes an x-ray scanner gantry, an intermediate gear, a first actuator, a motor gear, a motor, a second actuator and a control module. The gantry includes: a housing; a gantry gear formed as part of or connected to the housing; a rotor; a generator mounted on the rotor; and a first generator gear and a second generator gear connected to or configured to engage with one or more axles of the generator. The second generator gear is engaged with the gantry gear. The first actuator is connected to the intermediate gear. The motor gear is coupled to and configured to rotate the intermediate gear. The motor is configured to rotate the motor gear. The second actuator is configured to actuate the motor gear to engage the motor with the rotor. The control module is configured to operate in a first mode and a second mode. The control module is configured to: while in the first mode, engage the intermediate gear to the first generator gear via the first actuator to rotate, via the motor gear, the intermediate gear and as a result the first generator gear to generate power; and while in the second mode, engage the motor to the rotor via the second actuator to rotate, via the motor gear, the rotor and as a result the second generator gear to generate power.

In other features, a system is provided and includes an x-ray scanner gantry, a motor gear, a motor, a first actuator, and a control module. The gantry includes: a housing; a gantry gear formed as part of or connected to the housing; a rotor; a generator connected to the rotor; and a first generator gear connected to an axle of the generator. The first generator gear is engaged with the gantry gear. The motor is configured to rotate the motor gear. The first actuator is configured to actuate the motor gear to engage the motor with the rotor. The control module is configured to operate in a first mode and a second mode. The control module is configured to: while in the first mode, translate the motor gear to disengage the motor from the rotor and turn OFF the generator; and while in the second mode, (i) translate the motor gear via the first actuator to engage the motor to the rotor, and (ii) rotate, via the motor gear, the rotor and as a result the first generator gear to generate power.

In other features, a system is provided and includes an x-ray scanner gantry, an intermediate gear, a first actuator, a motor gear, a motor, a second actuator and a control module. The gantry includes: a rotor; a generator connected to the rotor; and a generator gear connected to an axle of the generator. The first actuator connected to the intermediate gear. The motor gear is coupled to and configured to rotate the intermediate gear. The motor is configured to rotate the motor gear. The second actuator is configured to actuate the motor gear to engage the motor with the rotor. The control module is configured to operate in a first mode and a second mode. The control module is configured to: while in the first mode, engage the intermediate gear to the generator gear via the first actuator to rotate, via the motor gear, the intermediate gear and as a result the generator gear to generate power; and while in the second mode, disengage the intermediate gear from the generator gear to turn OFF the generator.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
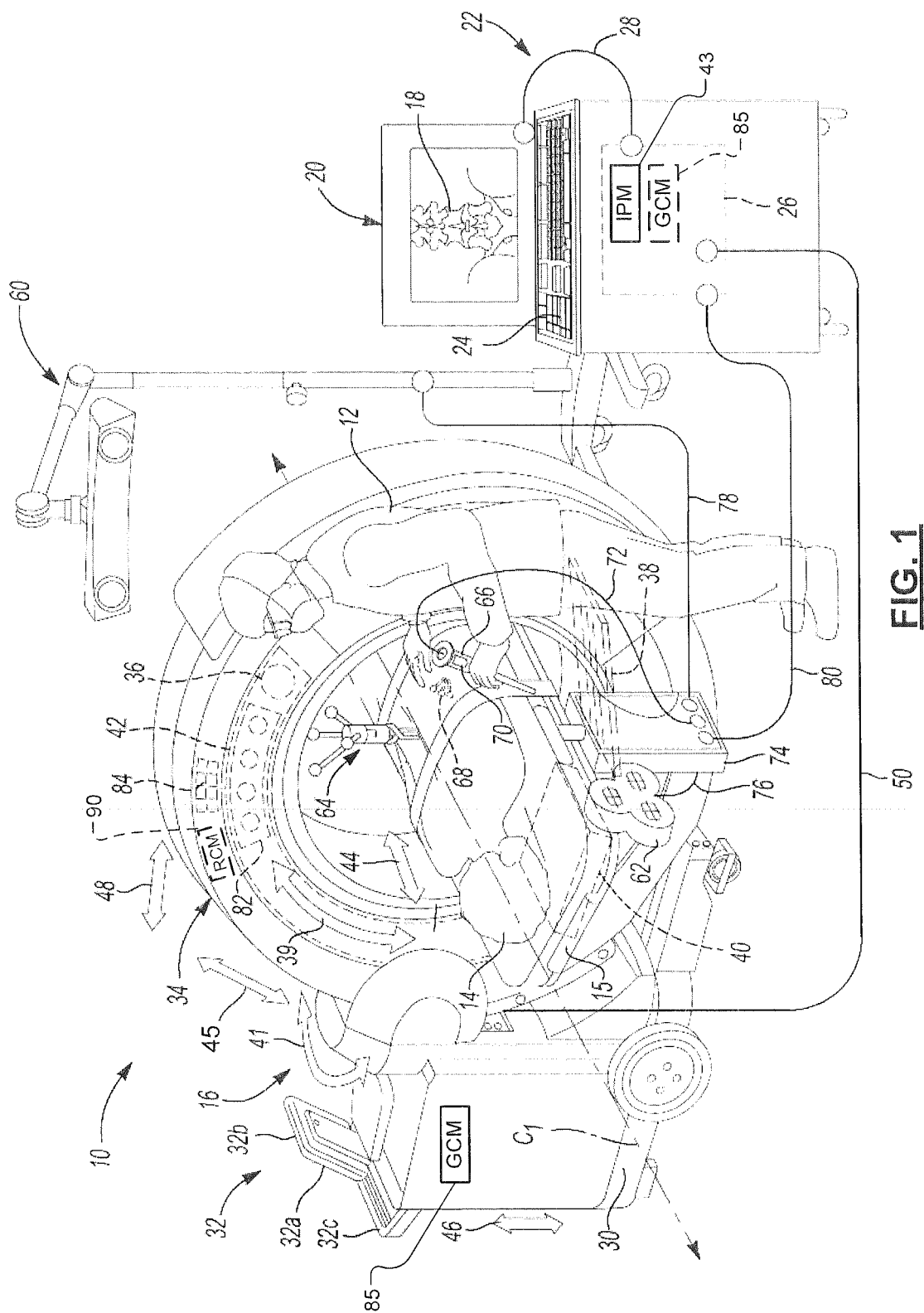
FIG. 1 is an environmental view of an imaging system in an operating theatre, including a rotor with a mechanically powered generator in accordance with an embodiment of the present disclosure.

To overcome the disadvantages associated with traditional imaging systems that have continuous rotation capable rotors, imaging system examples are disclosed herein, which each include a mechanically powered generator. The generators are mounted on or connected to respective rotors of the gantries. The disclosed imaging systems are less complex, less expensive, and require less maintenance than the imaging systems including slip rings and inductive coupling devices to transfer power to devices on a rotor of a gantry.

The following description is merely exemplary in nature. It should be understood that throughout the drawings, corresponding reference numerals indicate like or corresponding parts and features. As indicated above, the present teachings are directed toward an imaging system, such as an O-Arm or C-Arm imaging system. It should be noted, however, that the teachings disclosed herein are applicable to other imaging systems.

FIG. 1 shows an operating theatre (or inside of an operating room) 10 and a user 12 (e.g., a physician) performing a procedure on a subject (e.g., a patient) 14. In performing the procedure, the user 12 uses an imaging system 16 to acquire image data of the patient 14. The image data acquired of the patient 14 can include two-dimensional (2D) or three-dimensional (3D) images. Models may be generated using the acquired image data. The model can be a three-dimension (3D) volumetric model generated based on the acquired image data using various techniques, including algebraic iterative techniques. The image data (designated 18) can be displayed on a display device 20, and additionally, may be displayed on a display device 32a associated with an imaging computing system 32. The displayed image data 18 may include 2D images, 3D images, and/or a time changing 4D images. The displayed image data 18 may also include acquired image data, generated image data, and/or a combination of the acquired and generated image data.

Image data acquired of a patient 14 may be acquired as 2D projections. The 2D projections may then be used to reconstruct 3D volumetric image data of the patient 14. Also, theoretical or forward 2D projections may be generated from the 3D volumetric image data. Accordingly, image data may be used to provide 2D projections and/or 3D volumetric models.

The display device 20 may be part of a computing system 22. The computing system 22 may include a variety of computer-readable media. The computer-readable media may be any available media that is accessed by the computing system 22 and may include both volatile and non-volatile media, and removable and non-removable media. By way of example, the computer-readable media may include computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors may include multiple-processing core processors, microprocessors, etc.) that may be incorporated with the computing system 22. The input device 24 may include any suitable device to enable a user to interface with the computing system 22, such as a touchpad, touch pen, touch screen, keyboard, mouse, joystick, trackball, wireless mouse, audible control or a combination thereof. Furthermore, while the computing system 22 is described and illustrated herein as comprising the input device 24 discrete from the display device 20, the computing system 22 may include a touchpad or tablet computing device and may be integrated within or be part of the imaging computing system 32. A connection (or communication line) 28 may be provided between the computing system 22 and the display device 20 for data communication to allow driving the display device 20 to illustrate the image data 18.

The imaging system 16 may be an O-Arm imaging system, a C-Arm imaging system or other suitable imaging system. The imaging system 16 may include a mobile cart 30, the imaging computing system 32 and a gantry 34 (or x-ray scanner gantry). The gantry 34 includes an x-ray source 36, a collimator (not shown), a multi-row detector 38, a flat panel detector 40 and a rotor 42. With reference to FIG. 1, the mobile cart 30 may be moved from one operating theater or room to another and the gantry 34 may be moved relative to the mobile cart 30. This allows the imaging system 16 to be mobile and used for various procedures without requiring a capital expenditure or space dedicated to a fixed imaging system. Although the gantry 34 is shown as being mobile, the gantry 34 may not be connected to the mobile cart 30 and may be in a fixed position.

The gantry 34 may define an isocenter of the imaging system 16. In this regard, a centerline C1 through the gantry 34 defines an isocenter or center of the imaging system 16. Generally, the patient 14 can be positioned along the centerline C1 of the gantry 34, such that a longitudinal axis of the patient 14 is aligned with the isocenter of the imaging system 16.

The imaging computing system 32 may control the movement, positioning and adjustment of the multi-row detector 38, the flat panel detector 40 and the rotor 42 independently to enable image data acquisition via an image processing module 43 of the processor 26. The processed images may be displayed on the display device 20.

During operation, the source 36 emits x-rays through the patient 14, which are detected by the multi-row detector 38 or the flat panel detector 40. The x-rays emitted by the source 36 may be shaped by the collimator and emitted for detection by the multi-row detector 38 or the flat panel detector 40. The collimator may include one or more leaves, which may be controlled to shape the x-rays emitted by the source 36. The collimator may shape the x-rays emitted by the source 36 into a beam that corresponds with the shape of the multi-row detector 38 and the flat panel detector 40. The multi-row detector 38 may be selected to acquire image data of low contrast regions of the anatomy, such as regions of soft tissue. The flat panel detector 40 may be selected to acquire image data of high contrast regions of the anatomy, such as bone. The source 36, the collimator, the multi-row detector 38 and the flat panel detector 40 may each be coupled to and/or mounted on the rotor 42.

The multi-row detector 38 and the flat panel detector 40 may be coupled to the rotor 42 to be (i) diametrically opposed from the source 36 and the collimator within the gantry 34, and (ii) independently movable relative to each other and into alignment with the source 36 and the collimator. In one example, the multi-row detector 38 may be positioned such that the flat panel detector 40 may be adjacent to the multi-row detector 38. In one alternative example, the flat panel detector 40 may be moved over the multi-row detector 38 into alignment with the source 36 when an image using the flat panel detector 40 is acquired. In another example, the multi-row detector 38 may be positioned over the flat panel detector 40. As a further alternative, the multi-row detector 38 and the flat panel detector 40 may each be separately movable, such that the selected multi-row detector 38 or flat panel detector 40 may be aligned with the source 36 and the collimator. The selected one of the multi-row detector 38 and the flat panel detector 40 may be aligned with the source 36 and the collimator when the selected one of the multi-row detector 38 and the flat panel detector 40 is substantially opposite or about 180 degrees apart from the source 36 and the collimator.

As the source 36, collimator, multi-row detector 38 and flat panel detector 40 are coupled to the rotor 42, the source 36, flat panel detector 40 are movable within the gantry 34 about the patient 14. Thus, the multi-row detector 38 and the flat panel detector 40 are able to be rotated in a 360° motion around the patient 14, as indicated by arrow 39. The source 36 and collimator may move in concert with at least one of the multi-row detector 38 and the flat panel detector 40 such that the source 36 and collimator remain generally 180° apart from and opposed to the multi-row detector 38 or flat panel detector 40.

The gantry 34 has multiple degrees of freedom of motion. The gantry 34 may be isometrically swayed or swung (herein also referred to as iso-sway) relative to table 15 on which the patient 14 is disposed. The isometric swing is indicated by arrow 41. The gantry 34 may be: tilted relative to the patient 14 (as indicated by arrow 45); moved longitudinally relative to the patient 14 (as indicated by arrow 44); moved up and down relative to the mobile cart 30 and transversely to the patient 14 (as indicated by arrow 46); and moved away from or towards the mobile cart 30 (as indicated by arrow 48). These different degrees of freedom of motion of the gantry 34 allow the source 36, collimator, multi-row detector 38 and flat panel detector 40 to be positioned relative to the patient 14.

The imaging system 16 may be precisely controlled by the imaging computing system 32 to move the source 36, collimator, the multi-row detector 38 and the flat panel detector 40 relative to the patient 14 to generate precise image data of the patient 14. In addition, the imaging system 16 may be connected with the processor 26 via connection 50 which includes a wired or wireless connection or physical media transfer from the imaging system 16 to the processor 26. Thus, image data collected with the imaging system 16 may also be transferred from the imaging computing system 32 to the computing system 22 for navigation, display, reconstruction, etc.

The imaging system 16 may also be used during an unnavigated or navigated procedure. In a navigated procedure, a localizer, including either or both of an optical localizer 60 and an electromagnetic localizer 62, may be used to generate a field or receive or send a signal within a navigation domain relative to the patient 14. If desired, the components associated with performing a navigated procedure may be integrated within the imaging system 16. The navigated space or navigational domain relative to the patient 14 may be registered to the image data 18 to allow registration of a navigation space defined within the navigational domain and an image space defined by the image data 18. A patient tracker (or a dynamic reference frame) 64 may be connected to the patient 14 to allow for a dynamic registration and maintenance of the registration of the patient 14 to the image data 18.

An instrument 66 may then be tracked relative to the patient 14 to allow for a navigated procedure. The instrument 66 may include an optical tracking device 68 and/or an electromagnetic tracking device 70 to allow for tracking of the instrument 66 with either or both of the optical localizer 60 or the electromagnetic localizer 62. The instrument 66 may include a communication line 72 with a navigation interface device 74, which may communicate with the electromagnetic localizer 62 and/or the optical localizer 60. The navigation interface device 74 may then communicate with the processor 26 via a communication line 80. The connections or communication lines 28, 50, 76, 78, or 80 can be wire based as shown or the corresponding devices may communicate wirelessly with each other. The imaging system 16 tracks the instrument 66 relative to the patient 14 to allow for illustration of the tracked location of the instrument 66 relative to the image data 18 for performing a procedure.

The instrument 66 may be an interventional instrument and/or an implant. Implants may include a ventricular or vascular stent, a spinal implant, neurological stent or the like. The instrument 66 may be an interventional instrument such as a deep brain or neurological stimulator, an ablation device, or other appropriate instrument. Tracking the instrument 66 allows for viewing the location of the instrument 66 relative to the patient 14 with use of the registered image data 18 and without direct viewing of the instrument 66 within the patient 14. For example, the instrument 66 may be graphically illustrated as an icon superimposed on the image data 18.

Further, the imaging system 16 may include a tracking device, such as an optical tracking device 82 or an electromagnetic tracking device 84 to be tracked with a respective optical localizer 60 or the electromagnetic localizer 62. The tracking devices 82, 84 may be associated directly with the source 36, multi-row detector 38, flat panel detector 40, rotor 42, the gantry 34, or other appropriate part of the imaging system 16 to determine the location or position of the source 36, multi-row detector 38, flat panel detector 40, rotor 42 and/or gantry 34 relative to a selected reference frame. As illustrated, the tracking devices 82, 84 may be positioned on the exterior of the housing of the gantry 34. Accordingly, portions of the imaging system 16 including the instrument 66 may be tracked relative to the patient 14 to allow for initial registration, automatic registration or continued registration of the patient 14 relative to the image data 18.

The image processing module 43 may receive user input data from the input device 32c and may output the image data 18 to the display device 20 or the display device 32a. The user input data may include a request to acquire image data of the patient 14. Based on the user input data, the image processing module 43 may generate a detector signal and a motion signal. The detector signal may include a selected detector for image acquisition. The motion signal may include a motion profile for the rotor 42 to move to a selected location to acquire image data. The motion signal may be a command or instruction signal that is provided from the image processing module to a gantry control module 85. The gantry control module 85 may be included in the imaging computing system 32, on the mobile cart 30, or as part of the processor 26. The image processing module 43 may also send a source signal to the source 36. The source signal may command the source 36 to output or emit at least one or more x-ray pulses. The image processing module 43 may also send a collimator signal to the collimator. The collimator signal may indicate a selected shape of one or more collimated x-ray pulses. The selected shape of the collimated x-ray pulses may correspond to the selected one of the multi-row detector 38 and the flat panel detector 40. In this regard, if the multi-row detector 38 is selected, the collimated x-ray pulses may be shaped by the collimator to match the shape of the multi-row detector 38. If the flat panel detector 40 is selected, then the collimated x-ray pulses may be shaped by the collimator to match the shape of the flat panel detector 40.

The image processing module 43 may also receive as input a multi-row detector signal, which may include the one or more collimated x-ray pulses detected by the multi-row detector 38. The image processing module 43 may receive as input a flat panel detector signal, which may include the one or more collimated x-ray pulses detected by the flat panel detector 40. Based on the received collimated x-ray pulses, the image processing module 43 may generate the image data 18.

In one example, the image data 18 may include a single 2D image. In another example, the image processing module 43 may perform automatic reconstruction of an initial 3D model of an area of interest of the patient 14. Reconstruction of the 3D model may be performed in any appropriate manner, such as using algebraic techniques for optimization. The algebraic techniques may include Expectation maximization (EM), Ordered Subsets EM (OS-EM), Simultaneous Algebraic Reconstruction Technique (SART) and total variation minimization. A 3D volumetric reconstruction may be provided based on the 2D projections.

The algebraic techniques may include an iterative process to perform a reconstruction of the patient 14 for display as the image data 18. For example, a pure or theoretical image data projection, based on or generated from an atlas or stylized model of a "theoretical" patient, may be iteratively changed until the theoretical projection images match the acquired 2D projection image data of the patient 14. Then, the stylized model may be appropriately altered as the 3D volumetric reconstruction model of the acquired 2D projection image data of the patient 14 and may be used in a surgical intervention, such as navigation, diagnosis, or planning interventions. In this regard, the stylized model may provide additional detail regarding the anatomy of the patient 14, which may enable the user 12 to plan the surgical intervention efficiently. The theoretical model may be associated with theoretical image data to construct the theoretical model. In this way, the model or the image data 18 may be built based upon image data acquired of the patient 14 with the imaging system 16. The image processing module 43 may output the image data 18 to the display device 32a.

The gantry control module 85 may receive as an input the detector signal and the motion signal from the image processing module 43. The gantry control module 85, based on the detector signal and the motion signal may transmit (via wires or wirelessly) control signals to a rotor control module 90. The rotor control module 90 may be located on the rotor 42. Based on the detector signal, the gantry control module 85 may generate a first move signal to move the selected one of the multi-row detector 38 or the flat panel detector 40 into alignment with the source 36 and the collimator. Based on the motion signal, the gantry control module 85 may also generate a second move signal for the rotor 42 to move or rotate the rotor 42 within the gantry 34 relative to the patient 14. A third move signal may be generated based on the motion signal and provided to the rotor control module 90. The rotor 42 may be rotated to move the source 36, the collimator, the multi-row detector 38 and the flat panel detector 40 360° around the longitudinal axis of the patient 14 within the gantry 34. The rotor may be continuously rotated in a single direction more than 360°. The movement of the source 36, the collimator, the multi-row detector 38 and the flat panel detector 40 about the patient 14 may be controlled to acquire image data at selected locations and orientations relative to the patient 14. The gantry control module 85 and the rotor control module 90 are further described below with respect to FIGS. 2-4.

The 2D image data may be acquired at each of multiple annular positions of the rotor 42. The 3D image data may be generated based on the 2D image data. Also, the gantry 34, the source 36, the multi-row detector 38 and the flat panel detector 40 may not be moved in a circle, but rather may be moved in another pattern, such as a spiral helix, or other rotary movement about or relative to the patient 14. This can reduce exposure of a patient to radiation. The pattern (or path) may be non-symmetrical and/or non-linear based on movements of the imaging system 16, such as the gantry 34. In other words, the path may not be continuous in that the gantry 34 may be stopped and moved back in a direction along the path the gantry 34 previously followed. This may include following previous oscillations of the gantry 34.

Inputs to the imaging system 16 may be received at the input device 32c, input device 24, or other control modules (not shown) within the computing system 22 or imaging computing system 32, and/or determined by other sub-modules (not shown) within the image processing module 43. The image processing module 43 may receive user input data requesting that image data of the patient 14 be acquired. The input data may include information as to whether the region of interest on the patient 14 is a high contrast region (e.g. boney tissue) or a low contrast region (e.g. soft tissue). In one example, the user input data may include a region of interest on the anatomy of the patient 14. The image processing module 43 may automatically determine to use the multi-row detector 38 or the flat panel detector 40 based on the region of interest. For example, the user may select (i) the multi-row detector 38 to acquire an image of soft tissue, and (ii) the flat panel detector 40 to acquire an image of boney tissue.

Based on the user input data, the image processing module 43 may generate source data and detector type data. The image processing module 43 may also generate motion profile data and collimator data. The source data may include information to output x-ray pulses or a signal to power-down the imaging system 16. The detector type data may include the selected multi-row detector 38 or flat panel detector 40 to acquire the image data. The motion profile data may include a selected profile for the movement of the rotor 42 within the gantry 34. The collimator data may include information to shape the x-ray pulses into collimated x-ray pulses to match the selected one of the multi-row detector 38 and flat panel detector 40.

The image processing module 43 may also receive as an input multi-row detector data and flat panel detector data. The multi-row detector data may indicate the energy from the collimated x-ray pulses received by the multi-row detector 38. The flat panel detector data may indicate the energy from the collimated x-ray pulses received by the flat panel detector 40. Based on the multi-row detector data and the flat panel detector data, the image processing module 43 may generate the image data 18 and may output this image data 18 to the display device 32a or display device 20.

The gantry control module 85 may receive as input the detector type data and the motion profile data. Based on the detector type data, the gantry control module 85 may generate flat panel move data or multi-row move data (and/or corresponding signals). The flat panel move data may include a selected position for the flat panel detector 40 to move to in order to be aligned with the source 36 and collimator. The multi-row move data may include a selected position for the multi-row detector 38 to move in order to be aligned with the source 36 and collimator.

The processor 26 or a module thereof, based on the source data, may cause the source 36 to generate pulse data for control of the collimator. The pulse data may include pulse data for at least one x-ray pulse. The processor 26 and/or a module thereof may receive as an input the multi-row move data and the collimated pulse data. Based on the multi-row move data, the multi-row detector 38 may move into alignment with the source 36. Based on the received pulse data, the processor 26 and/or a module thereof may generate the multi-row detector data (and/or a corresponding signal) for the image processing module 43. The processor 26 and/or a module thereof may receive as an input the flat panel move data and the collimated pulse data. Based on the flat panel move data, the flat panel detector 40 may move into alignment with the source 36. Based on the received pulse data, the flat panel control module may generate the flat panel detector data (and/or a corresponding signal) for the image processing module 43.

Based on the motion profile data, the gantry control module 85 may generate rotor move data (and/or a corresponding signal) for the rotor control module 90. The rotor move data may indicate a selected movement profile for the rotor 42 to move within the gantry 34 to enable the acquisition of the image data. The rotor control module 90 may receive as an input the rotor move data. Based on the rotor move data, the rotor 42 may be moved within the gantry 34 to a desired location in order to acquire the image data.

Figure 2:
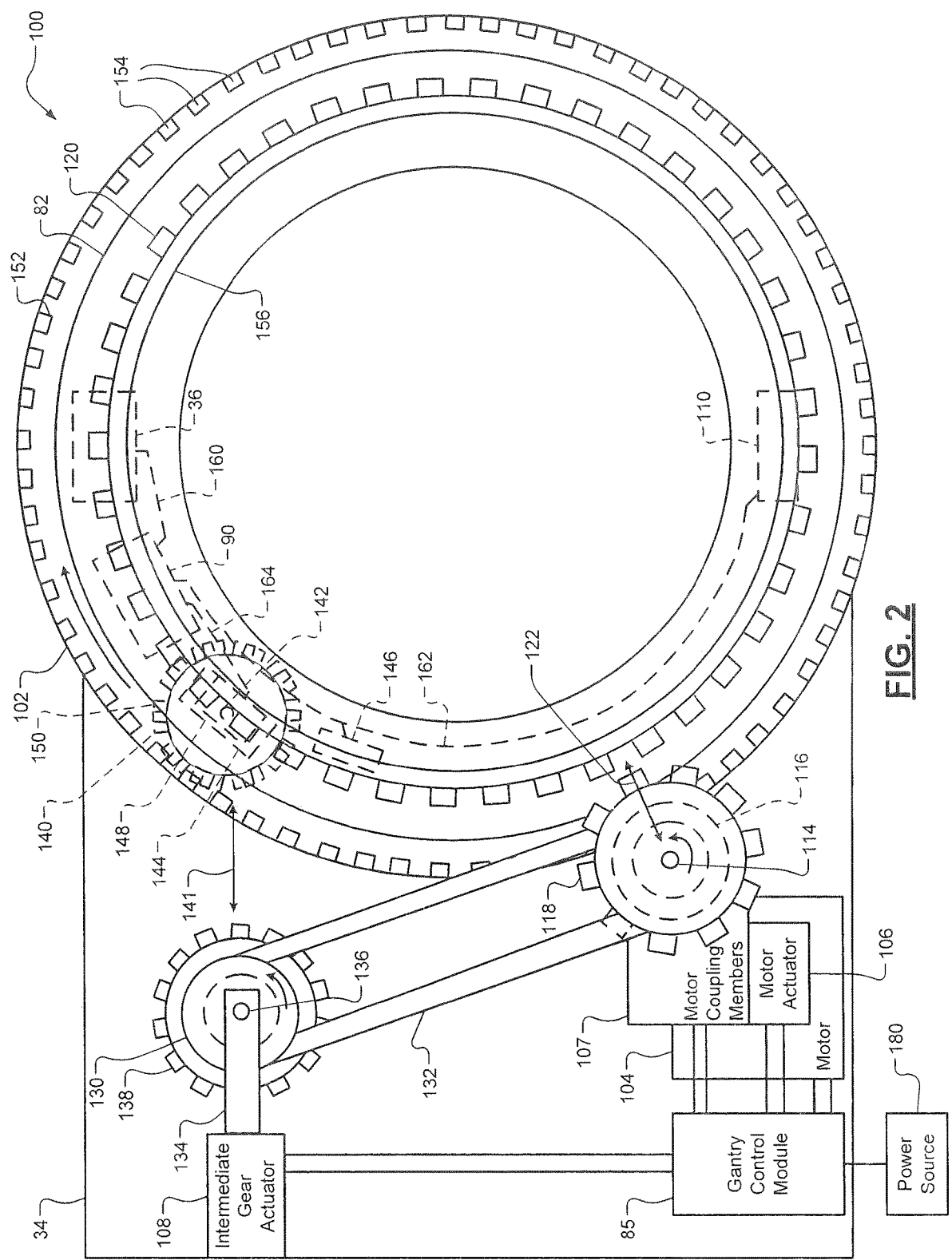
FIG. 2 is functional block diagram and side view of a portion of the imaging system of FIG. 1.

FIG. 2 shows a portion 100 of the imaging system 16 of FIG. 1. The portion 100 includes the gantry 34. FIG. 2 is shown for illustrative example purposes only. The gantry 34 and other components, devices, modules thereof, which are shown in FIG. 2 are not shown to scale and may have different form factors than that shown. The gantry 34 and the corresponding components, devices, modules may have different sizes and shapes than shown and may be in a different locations and configuration relative to each other than shown. Also, in the following description, various coupling and/or engagement devices and members are described. The coupling and/or engagement devices (e.g., gears, pulleys, belts, brackets, etc.) and members are provided as examples and for illustration purposes, other coupling and/or engagement devices and members may be used. The disclosed gears may each have various sizes, may have different ratios relative to each other, and may have different sizes and/or ratios than shown.

The gantry 34 includes an 'O'-shaped housing 102. A cross-sectional view of the 'O'-shaped housing 102 is shown in FIG. 2. The rotor 82 is disposed within the housing 102. Although the rotor 82 is shown as being 'O'-shaped, the rotor 82 may be 'C'-shaped. The rotor 82 may be, for example, spool-shaped or have other similar shape to allow components and devices to be mounted on a cylindrical portion of the rotor 82.

The portion 100 further includes the gantry control module 85, a motor 104, a motor actuator 106, motor coupling members 107, and an intermediate gear actuator 108. The actuators 106, 108 may include and/or be implemented as motors. The gantry control module 85 controls operation of the motor 104, the motor actuator 106 and the intermediate gear actuator 108. The motor actuator 106 may be powered by and controlled by the gantry control module 85. The motor actuator may move the motor gear 118 as shown or may be separate from the motor 104 and move the motor 104 and the motor gear 118. The coupling members 107 couple the motor 104 and/or the motor actuator 106 to the motor gear 118. The coupling members 107 may include brackets, clamps, hinges, gears, pulleys, belts, chains, etc. The portion 100 further includes the x-ray source 36, an x-ray detector 110 (e.g., one of the x-ray detectors 38, 40 of FIG. 1), the rotor control module 90, and a generator 144.

The gantry control module 85 may be in a sleep (or stand-by) mode or may be operated in a non-continuous rotation mode (sometimes referred to as a 2D imaging mode) or a continuous rotation mode (sometimes referred to as a 3D imaging mode). During the sleep mode, the rotor 82 of the gantry 34 is not rotating and the motor 104 is turned OFF and/or is not rotating a motor axle 114 of the motor 104. During the non-continuous mode, the motor 104 is ON, but is not engaged with the rotor 82. As a result, the rotor 82 is not rotating (or is stationary). The motor axle 114 is connected to a motor (or first) pulley 116 and a motor (or first) gear 118. The motor actuator 106 is used to engage the motor gear 118 to or disengage the motor gear 118 from a rotor gear 120 (as indicated by arrow 122). The rotor (or second) gear 120 is mounted on the rotor 82 and rotates with the rotor 82. During the non-continuous mode, the motor gear 118 is disengaged from the rotor gear 120.

The first pulley 116 may be connected to a second pulley 130 via first coupling member 132 (e.g., a belt, a chain, or other suitable coupling member). The second pulley 130 is connected to an intermediate gear actuator 108 via second coupling member 134 (e.g., a shaft, a bracket, or other suitable coupling member). The second coupling member 134 may include a second axle (or pin) 136 on which the second pulley 130 and an intermediate (or third) gear 138 are mounted. The first coupling member 132 rotates the second pulley 130, which rotated the intermediate gear 138. The second pulley 130 may be attached to the intermediate gear 138. The intermediate gear actuator 108 moves the second coupling member 134 to engage the intermediate gear 138 with or disengage the intermediate gear 138 from a first generator gear 140. Movement of the intermediate gear 138 towards and away from the first generator gear 140 is shown by arrow 141. The first generator gear 140 is mounted on and/or configured to engage with a generator axle 142 of a generator 144. The generator 144 may be directly connected to the rotor 82 or may be mounted on the rotor 82 via a bracket 148.

Figure 3:
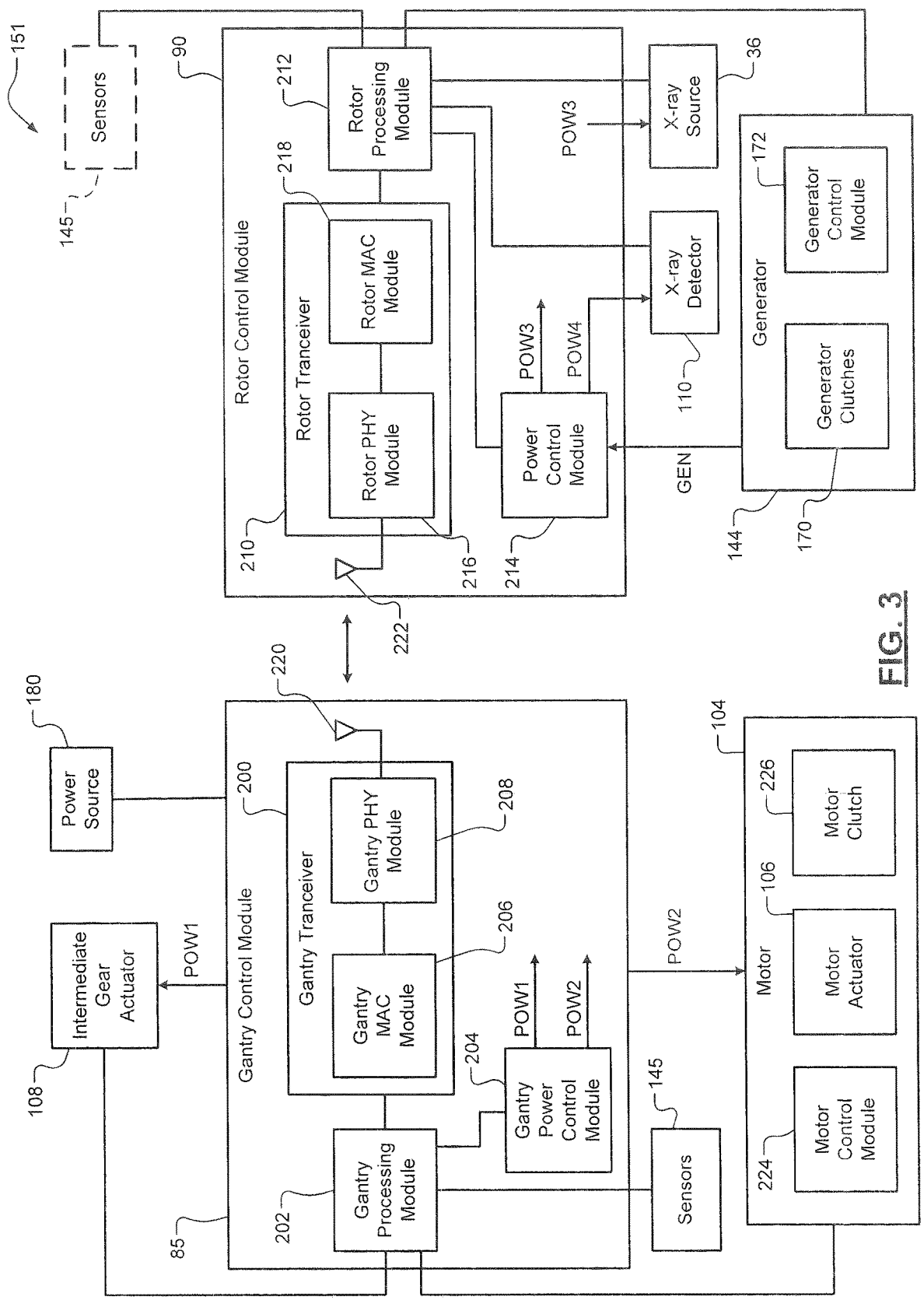
FIG. 3 is functional block diagram of a portion of the imaging system of FIG. 1.

The first generator gear 140 rotates the generator axle 142, which in turn causes the generator 144 to generate current to power the rotor control module 90, the source 36, the x-ray detector 110, sensors 145 (e.g., position, velocity and/or acceleration sensors) and/or other devices on the rotor 82. The sensors 145 are shown in FIG. 3. As an example, the sensors 145 may include an encoder 146. The encoder 146 may be used to detect a position, speed, velocity and/or acceleration of the rotor 82. Although the encoder 146 is shown as being mounted on the rotor 82 and connected to the rotor control module 90, the encoder may be mounted on the gantry 34 and may be connected to the gantry control module 85. The sensors 145 may be located on the rotor 82 or off of the rotor 82 and within the gantry 34.

A second generator gear 150 may also be connected to and/or mounted on the generator axle 142 or on another axle of the generator 144. The second generator gear 150 may always be engaged with a fixed (or fourth) non-rotating gear 152 (may be referred to as a "gantry gear"). The size of the second generator gear 150, the size of the teeth of the second generator gear 150 and the fourth gear 152, and the size of the fourth gear 152 may be adjusted to adjust a ratio between the gears 150, 152 and the rotating speed of the second generator gear 150 relative to the speed of the rotor 82 and/or the speed of the rotor gear 120. Additional intermediate gears may be connected between the gears 150, 152 to increase the rotating speed of the second generator gear 150 relative to the rotor 82 and/or the speed of the rotor gear 120. The fourth gear 152 may be formed as part of the housing 102 (as shown) or may be separate from, mounted on, and/or connected to the housing 102. The fourth gear 152 may always be indirectly engaged with the rotor gear 120 via the second generator gear 150 and thus may cause the second generator gear 150 to rotate when the rotor 82 is rotating. The generator 144 is moved in circular motion within the housing 102, which causes the second generator gear 150 to rotate and travel along the fourth gear 152 around the inside of the housing 102.

For illustrative purposes the generator gears 140, 150 are shown with dashed lines. This is because the generator gears 140, 150 may be in different locations relative to each other and relative to the rotor 82. The generator gears 140, 150 may be disposed on sides of the rotor 82, between the side walls of the rotor 82, and/or rotate within an opening in a cylinder of the rotor 82. For example, if the rotor is spool-shaped, the rotor 82 may have side walls and a center cylinder. The center cylinder may have a hole in which a portion of the gears 140, 150 rotate.

Although teeth 154 of the fourth gear 152 are shown as being external to (outside a periphery of) the rotor 82, the teeth 154 may be located internal to (within an inner diameter of) the rotor 82. If the teeth are located internal to the rotor 82, the teeth may be located, for example, internal to an inner cylindrical surface 156 of the rotor 82 and within the housing 102. The second generator gear 150 may also be located internal to the rotor 82 and travel on inner cylindrical surface 156. The internally located teeth may aid in maximizing the inner diameter of the rotor 82 and/or an inner diameter of the housing 102 in which a patient is positioned.

Rotation of the first generator gear 140 and/or the second generator gear 150 may cause the generator 144 to turn ON and/or generate current. The first generator gear 140 is rotating when the intermediate gear 138 is engaged with the first generator gear 140 and the motor gear 118 is rotating. The second generator gear 150 is rotating when (i) the motor gear 118 is engaged with the rotor gear 120, and (ii) the motor gear 118 is rotating.

The x-ray source 36, the x-ray detector 110, the generator 144 and the encoder 146 may be connected to the rotor control module 90 via wires 160, 162, 164. Although wires 160, 162, 164 are shown, the corresponding signals may be wirelessly transmitted between (i) the devices 36, 110, 144 146, and (ii) the rotor control module 90.

The generator 144 may include one or more generator clutches 170 (shown in FIG. 3) for engaging the axle(s) (e.g., the axle 142). This as a result engages the first generator gear 140 and/or the second generator gear 150, which causes the generator 144 to generate current.

During the non-continuous mode, the intermediate gear 138 is engaged with and rotating the first generator gear 140. Thus, during the non-continuous mode, the motor 104 is supplying mechanical energy to the generator 144 via the pulleys 116, 130, the first coupling member 132, the intermediate gear 138, and the first generator gear 140. The generator 144 then converts the mechanical energy to electrical energy to power the devices (e.g., the x-ray source 36, the rotor control module 90, and the x-ray detector 110, and/or the sensors 145) on the rotor 82. Note that the encoder may not be powered during the non-continuous mode, as the rotor 82 is not moving.

During the continuous mode, the intermediate gear 138 is disengaged from the first generator gear 140. During the continuous mode, the motor gear 118 is engaged with the rotor gear 120 and the rotor gear 120 rotates the second generator gear 150 due to engagement between the second generator gear 150 and the fourth gear 152. Thus, during the continuous mode, the motor 104 is transferring mechanical energy to the generator 144 via the motor gear 118, the rotor gear 120, and the second generator gear 150. The generator 144 then converts the mechanical energy to electrical energy to power the devices (e.g., the x-ray source 36, the rotor control module 90, the x-ray detector 110 and/or the sensors 145).

Although the generator gears are shown as being located external to the rotor gear 120 and teeth of the fourth gear 152 are shown as facing inward toward a center of the rotor 82, the teeth of the fourth gear 152 and/or the generator gears 140, 150 may be located within an inner diameter of the rotor 82. Also, although the teeth of the rotor gear 120 is shown as facing outward away from a center of the rotor 82, the teeth of the rotor gear 120 may face inward toward the center of the rotor 82 and the motor gear 118 may be translated accordingly to engage with the rotor gear 120.

The gantry control module 85 may receive power from a power source 180 and supply the power to the motor 104 and/or the intermediate gear actuator 108 based on the operating mode. The gantry control module 85 may control the actuators 106, 108 to engage and disengage the motor gear 118 and the intermediate gear 138. The motor gear 118 is not engaged to the rotor gear 120 when the intermediate gear 138 is engaged to the first generator gear 140 and vice versa.

Referring now also to FIG. 3, which shows another portion 151 of the imaging system 16 of FIG. 1. The portion 151 may include the x-ray source 36, the gantry control module 85, the rotor control module 90, the motor 104, the intermediate gear actuator 108, the x-ray detector 110, the generator 144 and the power source 180.

The gantry control module 85 may include a gantry transceiver 200, a gantry processing module 202 and a gantry power control module 204. The gantry transceiver 200 may include a gantry medium access control (MAC) module 206 and a gantry physical layer (PHY) module 208. The rotor control module 90 includes a rotor transceiver 210, a rotor processing module 212, and a rotor power control module 214. The rotor transceiver 210 includes a rotor PHY module 216 and a rotor MAC module 218.

The gantry processing module 202 may wirelessly communicate with the rotor processing module 212 via the transceivers 200, 210 and respective antennas 220, 222. The gantry processing module 202 may receive sensor signals and/or information from the sensors 145 directly or from the rotor control module 90. The gantry processing module 202 may control (i) power supplied to and/or position of the intermediate gear actuator 108, and/or (ii) power supplied to the motor 104 and/or position the motor actuator 106, and/or (iii) speed of the motor 104. The gantry processing module 202 may generate a mode signal, which is provided to the gantry power control module 204 and/or a motor control module 224 of the motor 104. The gantry power control module 204 may supply power to the actuators 106, 108 and the motor 104 based on the operating mode indicated by the mode signal. The power supplied to the intermediate gear actuator 108 and the motor 104 are shown as POW1 and POW2.

The motor 104 may include a motor clutch 226. The motor clutch 226 may be used to engage or disengage the motor axle 114 and thus the motor gear 118. When engaged, the motor gear 118 is rotating. The motor gear 118 may be engaged and rotating and not be engaged with the rotor 82.

The gantry MAC module 206 generates control signals based on data and/or information received from the gantry processing module 202. The gantry PHY module 208 wirelessly transmits the control signals to the rotor PHY module 216. The rotor MAC module 218 may generate information signals based on data and/or information received from the rotor processing module 212. The information signals are transmitted wirelessly via the rotor PHY module 216 to the gantry PHY module 208. The gantry processing module 202 may control operation of the devices (e.g., x-ray source 36, x-ray detector 110, generator 144, rotor power control module 214, etc.) based on the information signals. The information signals may include sensor signals and/or corresponding information.

The rotor processing module 212 may generate a mode signal, which may match the mode signal generated by the gantry processing module 202. The rotor power control module 214 may receive power from the generator 144 depending on the operating mode and as indicated by power signal GEN. The rotor power control module 214 may power the devices (e.g., x-ray source 36, x-ray detector 110, sensors 145, etc.) on the rotor 82 based on the operating mode. Power supplied to the x-ray source 36 and the x-ray detector 110 are shown as POW3 and POW4. The generator 144 may include a generator control module 172 and the one or more generator clutches 170. The generator control module 172 may control engagement of the generator clutches 170 to the one or more generator axles (e.g., the generator axle 142). Engagement of the generator clutches increases load on the rotor 82 or the intermediate gear 138, thereby increasing load on the motor gear 118 and the motor 104.

Figure 4:
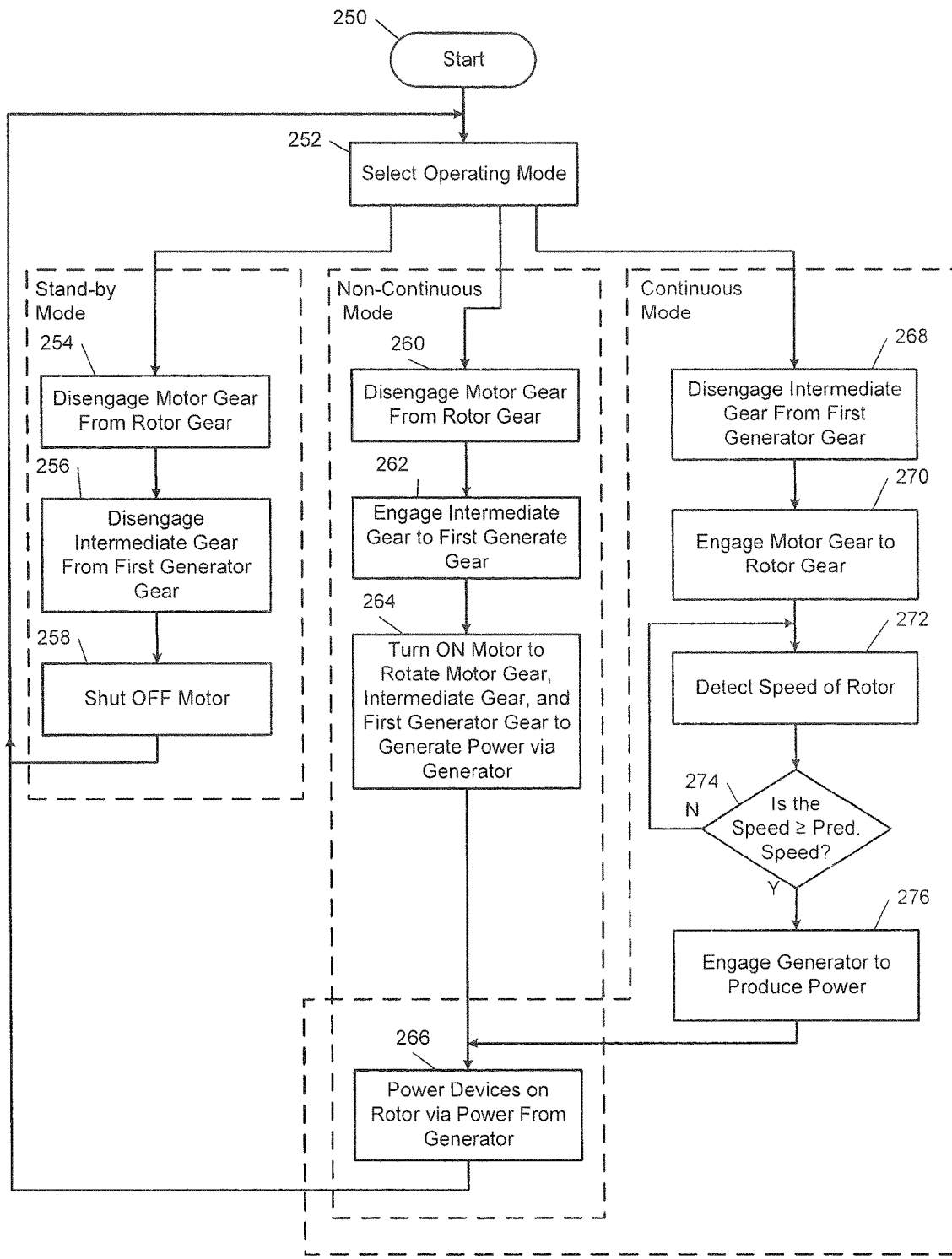
FIG. 4 illustrates a method of operating the imaging system in accordance with an embodiment of the present disclosure.

The imaging system 16 or a portion thereof may be operated using numerous methods, an example method is illustrated in FIG. 4. In FIG. 4, a method of operating an imaging system 16 or a portion thereof is shown. Although the following tasks are primarily described with respect to the implementations of FIGS. 1-3, the tasks may be easily modified to apply to other implementations of the present disclosure. The tasks may be iteratively performed.

The method may begin at 250. At 252, the gantry control module 85 and/or the gantry processing module 202 selects an operating mode. The operating mode may be the stand-by mode, the non-continuous mode, or the continuous mode. Depending on the operating mode, task 254, 260 or 268 may be performed subsequent to task 252.

At 254, the gantry control module 85 and/or the gantry processing module 202 operates in the stand-by mode and, if not already disengaged, the gantry control module 85 and/or the gantry processing module 202 disengages the motor gear 118 from the rotor gear 120 and thus disengages the motor 106 from the rotor 82. At 256, if not already disengaged, the gantry control module 85 and/or the gantry processing module 202 disengages the intermediate gear 138 from the first generator gear 140. At 258, the gantry control module 85 and/or the gantry processing module 202 shuts off the motor 104.

At 260, the gantry control module 85 and/or the gantry processing module 202 operate in the non-continuous mode and, if not already disengaged, the gantry control module 85 and/or the gantry processing module 202 disengages the motor gear 118 from the rotor gear 120. At 262, the gantry control module 85 and/or the gantry processing module 202 engages the intermediate gear 138 to the first generator gear 140. This includes powering the intermediate gear actuator 108 and moving the intermediate gear 138 towards and to engage with the first generator gear 140.

At 264, the gantry control module 85 and/or the gantry processing module 202 turns ON the motor 104 to rotate the motor gear 118, the coupling member 132, the intermediate gear 138, and the first generator gear 140. At 266, the generator 144 is engaged, reduces mechanical energy and generates power based on the rotation of the first generator gear 140. The power is supplied to the devices on the rotor 82.

At 268, the gantry control module 85 and/or the gantry processing module 202 operate in the continuous mode and, if not already disengaged, disengages the intermediate gear 138 from the first generator gear 140. At 270, the gantry control module 85 and/or the gantry processing module 202 engages the motor gear 118 to the rotor gear 120.

At 272, the rotor processing module 212 and/or the gantry processing module 202 determines a speed of the rotor 82. At 274, if the speed is greater than a predetermined speed, then task 276 is performed. The predetermined speed may be associated with the generator 144 generating a sufficient amount of power to power the devices on the rotor 82. The generator 144 may be a high-voltage generator and may generate, when the generator axle 142 is up to speed, a predetermined voltage (e.g., 150 kV). The motor 104 outputs a predetermined amount of torque to both rotate the rotor 82 and spin the generator axle 142. At 276, one of the clutches 170 are engaged such that the second generator gear is providing mechanical energy to the generator 144. The generator 144 converts the mechanical energy to electrical power. Task 266 may be performed subsequent to task 276.

Although not shown in FIG. 4, the generator 144 may be disengaged if the speed of the rotor 82 decreases to be less than the predetermined speed. Thus, the generator 144 may not always be engaged and as a result load of the generator 144 may not always be on the motor 104. This limits the power needed from the motor 104 when initially spinning up the rotor 82. By first spinning the rotor 82 and then applying the load of the generator 144, the initial torque output of the motor 104 is reduced substantially. In addition, the weight of the rotor 82 and the components and devices on the rotor 82 act as a flywheel such that when the generator 144 is engaged the flywheel provides some of the energy needed to overcome the initial load of the generator 144.

Although not shown in FIG. 4 and subsequent to task 266, the gantry control module 85, the gantry processing module 202, or other module disclosed herein may initiate x-ray imaging and recording of x-ray data. This may include generating and displaying x-ray images and corresponding 3D models, as described above. 2D images may be acquired during the non-continuous mode. 2D and 3D images may be acquired and/or generated during the continuous mode.

Task 252 may be performed subsequent to any of tasks 258 and 266. The above-described tasks are meant to be illustrative examples; the tasks may be performed sequentially, synchronously, simultaneously, continuously, during overlapping time periods or in a different order depending upon the application. Also, any of the tasks may not be performed or skipped depending on the implementation and/or sequence of events.

The wireless communications described in the present disclosure can be conducted in full or partial compliance with IEEE standard 802.11-2012, IEEE standard 802.16-2009, IEEE standard 802.20-2008, and/or Bluetooth Core Specification v4.0. In various implementations, Bluetooth Core Specification v4.0 may be modified by one or more of Bluetooth Core Specification Addendums 2, 3, or 4. In various implementations, IEEE 802.11-2012 may be supplemented by draft IEEE standard 802.11ac, draft IEEE standard 802.11ad, and/or draft IEEE standard 802.11ah.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, various embodiments are disclosed herein. Although each of the embodiments are described as having certain features, any one or more of the features described with respect to any one embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Connections and/or relationships between elements (including circuit elements, non-circuit elements, modules, etc.) are described using various terms, including "connected," "engaged," "coupled," "adjacent," and "disposed." As an example, when a connection between first and second elements is described in the above disclosure, that connection can be a direct connection where no other intervening elements are present between the first and second elements, but can also be an indirect connection where intervening elements are present between the first and second elements. Other words used to describe a relationship between elements should be interpreted in a similar manner (e.g., "engaged" versus "directly engaged", "coupled" versus "directly coupled", etc.). When a first element is adjacent to a second element, the first element may be in contact with the second element or the first element may be spaced away from the second element without any intervening element between the first element and the second element. When a first element is between a second element and a third element, the first element may be directly connected to the second element and the third element (referred to as "directly between") or intervening elements may be connected (i) between the first element and the second element, and/or (ii) between the first element and the third element. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. An imaging system, comprising:
   a gantry housing;
   a rotor rotatably positioned within the gantry housing;
   a generator connected to the rotor and configured to generate power to power a plurality of power devices associated with the rotor;
   a generator gear connected to or configured to engage an axle of the generator; and
   an intermediate gear driven by a motor gear and configured to selectively engage with the generator gear;
   wherein upon the intermediate gear engaging the generator gear, the generator gear is configured to rotate the axle of the generator to generate power to power the plurality of devices associated with the rotor.

2. The imaging system of claim 1, further comprising:
   a gantry gear formed as part of or connected to the housing, wherein upon rotation of the rotor, the generator gear is caused to rotate by the gantry gear to generate power.

3. The imaging system of claim 2, further comprising a motor gear and a rotor gear, wherein the motor gear is configured to engage the rotor gear to cause the rotor to rotate relative to the gantry gear to generate power.

4. The imaging system of claim 1, wherein the intermediate gear is a rotating gear configured to engage with the generator gear to cause the generator gear to rotate to generate power.

5. The imaging system of claim 1, wherein the plurality of devices associated with the rotor include an x-ray source and an x-ray detector.

6. The imaging system of claim 1, further comprising a gantry control module configured to operate the imaging system in a first mode to generate 2D images and in a second mode to generate 3D images, wherein the rotor further includes a rotor module connected to the rotor configured to wirelessly transmit signals to the gantry control module.

7. The imaging system of claim 1, further comprising:
   an intermediate gear actuator configured to selectively engage or disengage the intermediate gear with the generator gear.

8. An imaging system, comprising:
   a gantry housing;
   a rotor rotatably positioned within the gantry housing;
   a generator connected to the rotor and configured to generate power to power a plurality of power devices associated with the rotor;
   a generator gear connected to or configured to engage an axle of the generator; and
   a gear configured to engage with the generator gear;
   a motor gear and a rotor gear, wherein the motor gear is configured to engage the rotor gear to cause the rotor to rotate relative to the gantry gear to generate power;
   wherein upon the gear engaging the generator gear, the generator gear is configured to rotate the axle of the generator to generate power to power the plurality of devices associated with the rotor;
   wherein the gear is a gantry gear formed as part of or connected to the housing, wherein upon rotation of the rotor, the generator gear is caused to rotate by the gantry gear to generate power;

wherein the generator gear includes a first generator gear and a second generator gear, the first generator gear engaged by the gantry gear and the second generator gear engaged by an intermediate gear driven by the motor gear.

9. The imaging system of claim 8, further comprising a control module configured to operate in a first mode and a second mode, wherein in the first mode, the motor gear engages the rotor gear to cause the first generator gear to rotate via the gantry gear, and wherein in the second mode, the intermediate gear engages the second generator gear and is driven by the motor gear to rotate the second generator gear to generate power.

10. An imaging system, comprising:
a gantry housing;
a rotor rotatably positioned within the gantry housing;
a generator connected to the rotor and configured to generate power to power a plurality of power devices associated with the rotor;
a generator gear connected to or configured to engage an axle of the generator; and
a gear configured to engage with the generator gear;
an intermediate gear actuator configured to removably engage the intermediate gear with the generator gear;
wherein upon the gear engaging the generator gear, the generator gear is configured to rotate the axle of the generator to generate power to power the plurality of devices associated with the rotor;
wherein the gear is a rotating gear configured to engage with the generator gear to cause the generator gear to rotate to generate power;
wherein the rotating gear is an intermediate gear driven by a motor gear.

11. The imaging system of claim 10, further comprising a motor gear actuator configured to move the motor gear into engagement with a rotor gear to cause the rotor to rotate.

12. The imaging system of claim 11, wherein the generator gear includes a first generator gear and a second generator gear, the first generator gear engages a gantry gear and causes rotation of the first generator gear upon the motor gear engaging the rotor gear to rotate the rotor relative to the gantry housing.

13. The imaging system of claim 12, wherein the intermediate gear is configured to engage the second generator gear to rotate the generator gear when the rotor is static relative to the gantry housing.

14. An imaging system, comprising:
a gantry housing;
a rotor rotatably positioned within the gantry housing;
a generator connected or engaged with the rotor and configured to power a plurality of devices associated with the rotor;
a motor gear configured to engage with and rotate the rotor;
a gantry control module configured to control the motor gear; and
a rotor module connected to the rotor and configured to wirelessly transmit information signals to the gantry control module regarding the rotor; and
a sensor mounted on the rotor and configured to generate a signal, wherein the rotor module is configured to, based on the signal, generate the information signal and wirelessly transmit the information signal to the gantry control module and wherein the gantry control module is configured to control the motor gear based on the information signal;
wherein upon the gantry control module actuating the motor gear, the rotor rotates relative to the gantry housing and the generator generates power to power the plurality of devices associated with the rotor.

15. The imaging system of claim 14, further comprising a gantry gear formed as part of or connected to the housing and a generator gear connected to the generator, wherein upon the motor gear rotating the rotor, the generator gear engages the gantry gear to generate power.

16. The imaging system of claim 15, further comprising a rotor gear connected to the rotor and configured to be engaged by the motor gear, wherein upon actuation of the motor gear with a motor, the rotor rotates relative to the gantry gear and the generator gear is rotated by the gantry gear.

17. An imaging system, comprising:
a gantry housing;
a rotor rotatably positioned within the gantry housing;
a generator connected or engaged with the rotor and configured to power a plurality of devices associated with the rotor;
a motor gear configured to engage with and rotate the rotor;
a gantry control module configured to control the motor gear; and
a rotor module connected to the rotor and configured to wirelessly transmit information signals to the gantry control module regarding the rotor; and
a first generator gear and a second generator gear, wherein the control module when operating in a first mode utilizes the first generator gear and when operating in a second mode utilizes the second generator gear to generate power with the generator;
wherein upon the gantry control module actuating the motor gear, the rotor rotates relative to the gantry housing and the generator generates power to power the plurality of devices associated with the rotor.

18. A method for mechanically providing power to a generator on a continuously rotatable rotor of an imaging system, comprising:
rotating a motor gear to rotate the rotor;
rotating a first generator gear associated with the generator upon rotating the rotor to generate power in a first mode; and
rotating a second generator gear associated with the generator when the rotor is not rotating to generate power in a second mode.

19. The method of claim 18, further comprising:
moving the motor gear from a first position to a second position to engage a rotor gear to rotate the rotor and generate power in the first mode; and
moving the motor gear to the first position and moving an intermediate gear from a third position to a fourth position to engage and rotate the second generator gear to generate power in the second mode.

* * * * *